(12) United States Patent
Venard et al.

(10) Patent No.: US 9,421,563 B2
(45) Date of Patent: Aug. 23, 2016

(54) SELF-CONTAINED SPRAY APPARATUS FOR DISINFECTANTS

(71) Applicant: Karcher North America, Inc., Englewood, CO (US)

(72) Inventors: Daniel C. Venard, Centennial, CO (US); Ronald Matthew Forbes, Englewood, CO (US); Aaron J. May, Parker, CO (US)

(73) Assignee: Kärcher North America, Inc., Englewood, CO (US)

( * ) Notice: Subject to any disclaimer, the term of this patent is extended or adjusted under 35 U.S.C. 154(b) by 0 days.

(21) Appl. No.: 14/573,993

(22) Filed: Dec. 17, 2014

(65) Prior Publication Data

US 2015/0165459 A1   Jun. 18, 2015

Related U.S. Application Data

(60) Provisional application No. 61/916,938, filed on Dec. 17, 2013.

(51) Int. Cl.
| | |
|---|---|
| *B05B 7/30* | (2006.01) |
| *B05B 9/04* | (2006.01) |
| *B05B 9/00* | (2006.01) |
| *B05B 9/01* | (2006.01) |
| *A61L 2/22* | (2006.01) |
| *A61L 9/14* | (2006.01) |
| *B05B 15/06* | (2006.01) |

(52) U.S. Cl.
CPC ............... *B05B 9/0403* (2013.01); *A61L 2/22* (2013.01); *A61L 9/14* (2013.01); *B05B 9/007* (2013.01); *B05B 9/01* (2013.01); *A61L 2202/14* (2013.01); *A61L 2202/16* (2013.01); *A61L 2209/111* (2013.01); *B05B 15/068* (2013.01)

(58) Field of Classification Search
CPC ..... B05B 9/04; B05B 9/0403; B05B 9/0426; B05B 9/043; B05B 9/0861
USPC ................ 239/525, 526, 337, 349, 355, 360
See application file for complete search history.

(56) References Cited

U.S. PATENT DOCUMENTS

| | | | |
|---|---|---|---|
| 2,170,890 | A | 8/1939 | Allen |
| 2,896,862 | A | 7/1959 | Bede |
| 3,321,110 | A | 5/1967 | Price |

(Continued)

FOREIGN PATENT DOCUMENTS

| | | |
|---|---|---|
| CA | 1326983 | 2/1994 |
| EP | 0451942 | 10/1991 |

OTHER PUBLICATIONS

"UAC HA 10068C A/C Accumulator with Hose Assembly," retrieved from www.ebay.com/ctg/UAC-HA-10068C-A-C-Accumulator-Hose-Assembly-/79151059, retrieved on Dec. 4, 2013, 2 pages.

(Continued)

*Primary Examiner* — Davis Hwu
(74) *Attorney, Agent, or Firm* — Sheridan Ross P.C.

(57) ABSTRACT

A portable spray apparatus is provided. The apparatus is a self-contained portable unit having storage and dispensing capabilities for a fluid, including a disinfecting fluid. A pump and a pressure accumulator are provided in series and further connected to a spray gun or wand for dispensing a fluid. A detachable coupling allows a user to separate the pressure accumulator from the pump such that a user may spray disinfecting fluid in hard-to-reach areas.

20 Claims, 7 Drawing Sheets

(56) References Cited

U.S. PATENT DOCUMENTS

| | | | |
|---|---|---|---|
| 3,403,818 A | 10/1968 | Enssle | |
| 4,093,123 A | 6/1978 | Maran | |
| 4,678,010 A | 7/1987 | Purvis et al. | |
| 4,708,088 A | 11/1987 | Purvis et al. | |
| 5,478,015 A | 12/1995 | Black | |
| 5,735,461 A * | 4/1998 | Winther | B08B 3/026 137/115.15 |
| 6,158,669 A | 12/2000 | Louis | |
| 6,557,542 B1 | 5/2003 | Orr | |
| 6,565,015 B2 | 5/2003 | Leer et al. | |
| 6,695,228 B2 | 2/2004 | Odessa | |
| 6,981,613 B1 | 1/2006 | Kamisugi | |
| 8,047,455 B2 * | 11/2011 | Reedy | B05B 7/2416 239/296 |
| 2008/0001007 A1 * | 1/2008 | Gilpatrick | B05B 7/0408 239/310 |
| 2012/0226764 A1 | 9/2012 | Philip et al. | |
| 2012/0241537 A1 | 9/2012 | Schwei et al. | |

OTHER PUBLICATIONS

"Mobile 12 Volt accumulator-pressure cleaner," retrieved from http://www.frankana.de/search.do?search=Mobile+12+Volt+accumulator-pressure+cleaner, retrieved on May 4, 2015, 1 page.

"PurePak—Improving patient care and infection control, while reducing costs," PureTech Systems, 2 pages (Admitted prior art).

"PurePak—Providing More Complete Coverage, While Saving Time," PureTech Systems, 2 pages (Admitted prior art).

"PurePak—Frequently Asked Questions," PureTech Systems, 2 pages (Admitted prior art).

"PurePak—Effectively control the spread of infections," PureTech Systems, 1 page (Admitted prior art).

"PurePak—Operating Room Study," PureTech Systems, 25 pages (Admitted prior art).

"PurePak—Proposal," PureTech Systems, 27 pages (Admitted prior art).

"PureTech—Capabilities Summary," PureTech Systems, 1 page (Admitted prior art).

* cited by examiner

SELF-CONTAINED SPRAY APPARATUS FOR DISINFECTANTS

CROSS-REFERENCE TO RELATED APPLICATIONS

This application claims priority under 35 U.S.C. §119(e) to U.S. Provisional Patent Application Ser. No. 61/916,938 filed Dec. 17, 2013, which is incorporated herein in its entirety by reference.

FIELD OF THE INVENTION

The present invention relates generally to self-contained and portable devices for distributing a spray. More specifically, the present invention relates to self-contained and portable devices for applying a spray, preferably of a disinfectant or antibacterial variety.

BACKGROUND

The present invention generally relates to a disinfecting spray apparatus that can be utilized to sanitize equipment, surfaces, and devices, for example. More specifically, the present invention relates to a disinfecting spray apparatus that can be conveniently conveyed to various locations and provides features for a consistent spray distribution of at least one disinfecting material.

Spray bottle and aerosol containers are known to provide a spray, mist, and/or dispensation of a cleaning product. Such devices spray the disinfectant onto surfaces that are desired to be cleaned. Although a spray bottle is generally adequate to apply disinfectant to surfaces, the size of the spray bottle is limited and requires users to refill or replace the bottle frequently and/or carry multiple bottles on the housekeeping cart. Additionally, such devices do not generally apply the disinfectant/cleaner in a smooth, continuous pattern since a user must manually pump the spray bottle.

In addition to the limited supply of disinfectant that can be carried in a portable spray bottle, the distribution pattern of the disinfectant onto the surface to be cleaned is inconsistent and varied during the extended use of the spray bottle. The coverage and overall distribution of the disinfectant is affected by the type of nozzle used on the spray bottle and the action of the cleaning personnel utilizing the spray bottle.

One example of a spray apparatus that utilizes an electric pump is described in U.S. Patent Application Publication No. 2012/0241537 to Schwei et al., which is hereby incorporated by reference in its entirety. The device in Schwei comprises a tank, a pump, and a spray handle. However, the Schwei reference fails to disclose various novel features of the present invention as shown and described herein.

Therefore, a long-felt and unmet need exists for an improved system that provides a disinfectant in a more efficient manner.

SUMMARY OF THE INVENTION

Accordingly, the present invention contemplates a novel system, device, and method for a portable device capable of housing and distributing a relatively large volume of disinfectant material and provides the material to a surface in an efficient and predictable manner.

The present disclosure relates to a portable spray apparatus configured to apply any disinfectant or cleaner evenly and accurately over a desired surface. The disinfecting spray apparatus creates a fine spray that allows the solution to penetrate hard-to-reach surface areas and which dries in minutes. In various embodiments, disinfecting spray apparatuses are effective at applying a disinfectant to areas that may be overlooked with traditional methods of disinfectant.

In one embodiment, a disinfecting spray apparatus is provided that comprises an electric pump in communication with a power supply. The power supply preferably includes an on-board rechargeable battery. In one embodiment, the apparatus comprises a self-contained unit that can be conveyed (e.g. rolled via wheels) to various locations. In an alternative embodiment, the apparatus comprises a generally self-contained device that can be attached, secured, or mounted to various items, such as housekeeping carts or luggage carts.

In certain embodiments, a spray apparatus comprises a fluid storage container for clean fluid content that can be accessed from an external portion of the device to fill the container with any desired solution. In some embodiments, the fluid storage container is fixed to a chassis and/or body portion. In various embodiments, the fluid storage container may be selectively interconnected to a chassis and/or body portion such that a user may remove the fluid storage container and use other fluid storage containers with different qualities including different fluid content. Some embodiments of the present invention may include a plurality of fluid storage containers to provide a user with the option of selecting one or more of the fluid content in the plurality of fluid storage containers.

The disinfecting spray apparatus of certain embodiments the present disclosure includes a spray nozzle that creates a fine spray of the disinfectant while insuring that the disinfectant is not released in too fine of a mist. The selection of the nozzle design creates the desired droplet size and the desired pattern of coverage while controlling the size of the droplets to prevent the creation of an excessively fine of a mist, which may be inhaled.

In certain embodiments, a self-contained mobile spray apparatus for dispensing a fluid is provided. The apparatus, which is preferably provided for dispensing disinfecting or antibacterial solutions, comprises a chassis provided on wheels for ease of transport. The chassis comprises a fluid storage tank for housing a clean, unspent fluid, a pump which can be gravity-fed by the fluid storage tank, an accumulator in fluid communication with the pump, and a spray gun in fluid communication with the accumulator, the spray gun can be used to selectively dispense fluid. In various embodiments, the pump comprises an electric motor, the motor being powered by an on-board battery, which is preferably rechargeable.

In various embodiments, an accumulator is provided in fluid communication with a fluid dispensation device, such as a spray gun. In one embodiment, the accumulator is pressurized to approximately 110 PSI. It is contemplated that during use, the internal pressure of the accumulator drops during use and dispensation of the fluid. When the internal pressure of the accumulator drops to approximately 85 PSI, a pump is activated to recharge the internal pressure of the accumulator to approximately 110 PSI. Once the desired internal pressure is returned to the accumulator, the pump is deactivated, at least until recharging of the accumulator is again required. In this manner, the spray gun is allowed to operate continuously without substantial fluctuation or surges in pressure, or required down-time to allow the device to return to a desired pressure. The tank, pump, accumulator, and spray gun are preferably provided in series.

In certain embodiments, devices of the present invention are provided with tracking features, such as GPS and proximity tracking features, whereby the use, location, and related information of one or more devices can be tracked and counted. Such embodiments may be particularly desirable in hospital or sanitary settings wherein location of the device is often used to track important parameters.

Various devices are known to provide air powered atomization, which generally comprises passing a stream of compressed gas or air over a venturi to siphon a chemical or other additive into the air stream and where the additive is carried with the air stream. Such systems provide advantages of high spray quality, small droplet size, and longer spray distance. Disadvantages of such systems include increased weight of the sprayer, power source, require exchange of gas cylinders, adjustment of air regulators, adjust of product flow, noise, potential for noxious fumes, etc.

Alternatively, hydraulic atomization uses pressure to force fluid through a nozzle configured to create mists of varying droplet sizes. A hydraulic atomization system requires a pump that can provide the appropriate flow and pressure to match the nozzle flow rate. Spray characteristics, such as pattern shape and drop size, are determined by the nozzle configuration and fluid pressure. In various embodiments, a modified hydraulic system is provided and fitted with an air blower to project nozzle output and thus further reduce fall out and over spray.

One specific embodiment of the present invention comprises a portable spray apparatus for use in dispensing a fluid comprising: a body portion provided on a chassis; the chassis comprising a plurality of wheels adapted for conveying the apparatus; a clean fluid storage tank positioned at least partially within the body portion and having an internal volume to receive a fluid; and a pump provided within the body portion, the pump comprising a fluid inlet in fluid communication with the clean fluid storage tank and a pump outlet in fluid communication with an accumulator. In operation, an internal pressure of the accumulator is supplied by the pump, and the accumulator is associated with a device which maintains the internal pressure of the accumulator between approximately 50 PSI and 150 PSI. Then, the pump can withdraw fluid from the clean fluid storage tank. A supply hose extending from the body portion and having a first end is then in fluid communication with the accumulator to receive the fluid and a spray gun is connected to a second end of the supply hose. A spray nozzle is mounted to the spray gun and is sized to create a spray of fluid upon activation of the spray gun. Various embodiments of the present invention further comprise at least one sensor to monitor usage of the apparatus, a transmitter coupled to the at least one sensor, wherein the transmitter is configured to transmit data from the at least one sensor to a network; and a host system connected to the network and adapted to receive the at least one sensor data indicative of usage of the device.

Another specific embodiment of the present invention comprises a portable spray apparatus with detachable components comprising a clean fluid storage tank having an internal volume to receive a fluid; a pump comprising a fluid inlet in fluid communication with the clean fluid storage tank, and a pump outlet in fluid communication with an accumulator, wherein an internal pressure of the accumulator is supplied by the pump and the pump withdraws the fluid from the clean fluid storage tank upon activation; a detachable coupling is disposed between the pump outlet and the accumulator and has an attached state and a detached state, wherein in the attached state the coupling allows fluid communication between the pump outlet and the accumulator and in the detached state the coupling prevents fluid communication between the pump outlet and the accumulator. This embodiment also includes a supply hose having a first end which is in fluid communication with the accumulator to receive the fluid and a spray gun is connected to a second end with a spray nozzle mounted to the spray gun. The spray nozzle is sized to create a spray of fluid upon activation of the spray gun and the accumulator, supply hose, spray gun, and spray nozzle are separable from the pump when the coupling is in the detached state.

Yet another specific embodiment comprises a portable spray apparatus for use in dispensing a fluid comprising a body portion provided on a chassis which includes a plurality of wheels adapted for conveying the apparatus. A clean fluid storage tank is positioned at least partially within the body portion and has an internal volume to receive a fluid. A pump is provided within the body and has a fluid inlet in fluid communication with the clean fluid storage tank and an outlet in fluid communication with an accumulator. An internal pressure of the accumulator is supplied by the pump, and the accumulator is associated with a device which maintains the internal pressure of the accumulator between approximately 85 PSI and 110 PSI. The pump is designed to withdraw a fluid from the clean fluid storage tank upon activation which could occur in variety of ways. A rechargeable battery is provided within the body portion, and supplies power to the pump, wherein the rechargeable battery has a voltage rating, and the pump has a voltage rating, and wherein the battery voltage rating is approximately 33% of the pump voltage rating. A detachable coupling may also be disposed between the pump outlet and the accumulator and can have an attached state and a detached state, wherein in the attached state the coupling allows fluid communication between the pump outlet and the accumulator, and in the detached state the coupling prevents fluid communication between the pump outlet and the accumulator. A supply hose extending from the body portion and having a first end in fluid communication with the accumulator to receive the fluid can also be provided. A spray gun can be connected to a second end of the supply hose and a spray nozzle can be mounted to the spray gun, wherein the spray nozzle is sized to create a spray of fluid upon activation of the spray gun. In some embodiments, the accumulator, supply hose, spray gun, and spray nozzle are separable from the pump when the coupling is in the detached state.

Various other features, objects and advantages of the invention will be made apparent from the following description taken together with the drawings. Although various embodiments of the present invention are particularly well suited for dispensing disinfectant and antibacterial agents, it will be expressly recognized that the present invention is not so limited. Indeed, embodiments and devices of the present invention may be employed to dispense various fluids including, but not limited to, paint, pesticides, lubricants, pest control, fertilizers, etc. In preferred embodiments, however, the present invention is particularly well suited for touchless disinfecting.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

These and other advantages will be apparent from the disclosure of the invention(s) contained herein. The above-described embodiments, objectives, and configurations are neither complete nor exhaustive. As will be appreciated, other embodiments of the invention are possible using, alone or in combination, one or more of the features set forth above or described in detail below. Further, the summary of the invention is neither intended nor should it be construed as being representative of the full extent and scope of the present invention. The present invention is set forth in various levels of detail in the summary of the invention, as well as, in the attached drawings and the detailed description of the invention and no limitation as to the scope of the present invention is intended to either the inclusion or non-inclusion of elements, components, etc. in this summary of the invention. Additional aspects of the present invention will become more readily apparent from the detailed description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

To assist in the understanding of one embodiment of the present invention, the following list of components and associated numbering found in the drawings is provided herein:

| # | Component |
|---|---|
| 2 | Spray Apparatus |
| 4 | Body Portion |
| 6 | Caster Wheel |
| 8 | Clean Fluid Tank |
| 10 | Handle |
| 11 | Height-Adjustable Portion |
| 12 | Hose |
| 14 | Spray Gun |
| 16 | Switch |
| 18 | Port |
| 20 | Chassis |
| 22 | Frame Member |
| 24 | Pump Supply Line |
| 26 | Inlet |
| 28 | Pump |
| 30 | Accumulator |
| 32 | Internal Frame Structure |
| 34 | Pump Outlet |
| 36 | Accumulator Supply Line |
| 38 | Accumulator Inlet |
| 40 | Fluid Exit Line |
| 42 | Bottom Surface |
| 44 | Door |
| 46 | Accumulator Outlet |
| 48 | User-Grasping Portion |
| 50 | Fastener |
| 52 | Battery |
| 54 | Charger |
| 56 | Detachable Coupling |

DETAILED DESCRIPTION

The present invention has significant benefits across a broad spectrum of endeavors. To acquaint persons skilled in the pertinent arts most closely related to the present invention, a preferred embodiment of the method that illustrates the best mode now contemplated for putting the invention into practice is described herein by, and with reference to, the annexed drawings that form a part of the specification. The exemplary method is described in detail without attempting to describe all of the various forms and modifications in which the invention might be embodied. As such, the embodiments described herein are illustrative, and as will become apparent to those skilled in the arts, can be modified in numerous ways within the scope and spirit of the invention.

The detailed description is to be construed as exemplary only and does not describe every possible embodiment since describing every possible embodiment would be impractical, if not impossible. Numerous alternative embodiments could be implemented, using either current technology or technology developed after the filing date of this patent.

Referring now to FIGS. 1-7, a fluid distribution apparatus is provided according to various embodiments of the present invention. It should be understood that the drawings are not necessarily to scale. In certain instances, details that are not necessary for an understanding of the invention or that render other details difficult to perceive may have been omitted from these drawings. It should be understood, of course, that the invention is not limited to the particular embodiments illustrated in the drawings.

Figure 1:
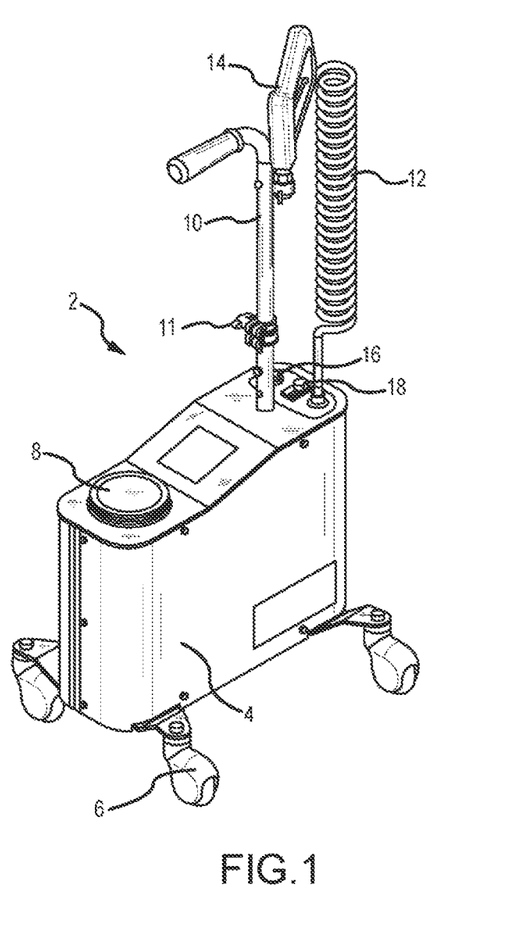
FIG. 1 is a front perspective view of a spray apparatus according to one embodiment of the present invention.

As shown in FIG. 1, a spray apparatus 2 is provided comprising a body portion 4, and a plurality of wheels 6 for conveying the device 2. A clean fluid tank 8 is provided and a portion of the tank 8 protrudes from the body portion 4 to allow ease of access for filling the tank 8. In the depicted embodiment, the tank 8 comprises a cap that is selectively removable to access the tank. The cap and upper portion of the tank extend through an upper surface of the body portion 4. It will be recognized, however, that various alternative access means for filling the tank are provided, and the present invention is not limited to the particular embodiment depicted.

The spray apparatus 2 further comprises a handle 10 for grasping by a user and moving the device 2. As shown, the handle 10 comprises a height-adjustable portion 11 that allows a rigid vertical member and a user-portion for grasping to translate positions relative to each other. A hose 12 interconnects a spray gun 14 to various components of the device 2, as shown and described herein. An exterior surface of the body, or otherwise accessible portion of the body, comprises an on-off switch 16 and a port 18 for recharging an on-board battery. The port 18 is provided to accept one or more known battery recharging interfaces.

The port 18 may also provide network connectivity for the apparatus 2. For example, the apparatus 2 may keep track of various attributes or parameters during use. The apparatus 2 may relay this data to a network in real time via wireless connections commonly known in the art such as Wi-Fi, radio, RFID, cell phone networks, etc. The apparatus 2 may also provide this data via a hard connection such as a USB connection, 30 pin connector, or any other connector commonly known in the art. An example of networking multiple apparatuses may be found in US Patent Pub. 2012/0226764, which is incorporated herein in its entirety by reference.

The data collected by the apparatus 2 can aid the user in a number of ways. The apparatus 2 may keep track of its power levels, fluid levels in various reservoirs, its positions using a GPS or GPS-like technology, maintenance milestones after a predetermined threshold has been crossed, e.g., a period of time, battery cycles, distance traveled, etc.

Figure 2:
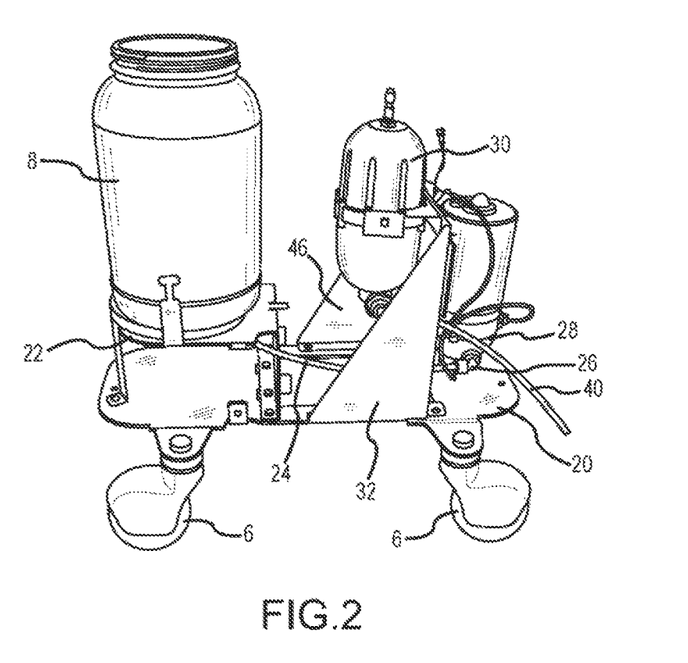
FIG. 2 is a side elevation view of a spray apparatus according to one embodiment of the present invention.

FIG. 2 is a side view of an apparatus 2 according to one embodiment of the present invention wherein certain portions, including the body, have been removed for illustration purposes. As shown, a chassis 20 is provided for supporting various features of the device 2. A plurality of wheels 6 are provided for conveying the device 2. The tank 8 is provided on a frame member 22, the frame member 22 comprising an elevated platform for supporting the tank 8. The tank 8 comprises a pump supply line 24 for supplying a fluid to a pump 28. Although the pump may comprise one or more of various different types of pumps, it is contemplated that in a preferred embodiment the pump comprises a 1.6 GPM, 36 Volt DC diaphragm pump pressurized to approximately 100-120 PSI. The pump is powered by a battery (not shown), which in various embodiments comprises a 12 Volt sealed rechargeable, valve regulated, lead acid battery, although various other batteries are contemplated, as will be recognized by one of ordinary skill in the art.

In one embodiment, a particular advantage of the present invention is to provide a combination of pump and battery wherein the voltage rating of the battery is less than the voltage rating of the pump. In one embodiment, the voltage rating of the battery is between approximately 20% to 50% of the voltage rating of the pump. In another embodiment, the voltage rating of the battery is approximately 33% of the voltage rating of the pump. In this configuration, the pump runs at slower speed than its maximum capacity and thereby extends the usable battery life of the device. The battery is provided on the chassis and/or within the body. For example, the battery may be positioned beneath the tank 8 and/or underneath and between the tank 8 and the accumulator 30. In alternative embodiments, the unit 2 is void of a battery and comprises a power cord directly connecting the pump 28 to an external power source.

As further shown in FIG. 2, a pump supply line 24 is provided for conveying fluid from the tank 8 to the pump 28. The pump supply line 24 preferably comprises a flexible conduit that connects the tank 8 to the pump 28 such that solution can be gravity fed to the pump 28. Although the line 24 is primarily gravity fed in a preferred embodiment, one of skill in the art will recognize that pressure differentials induced by the pump may further induce or cause fluid flow. A port is provided on a bottom portion of the tank 8, and the pump supply line 24 conveys fluid from the port to the pump and is connected thereto by any number of known fittings or couplings. The pump comprises an inlet 26 and an outlet and an accumulator supply line (see 34, 36 of FIG. 3) for supplying fluid to the accumulator 30. A fluid exit line 40 is provided on a downstream portion of the accumulator through which fluid is supplied to a hose and spray gun and ultimately dispensed to a surface or target object.

Figure 3:
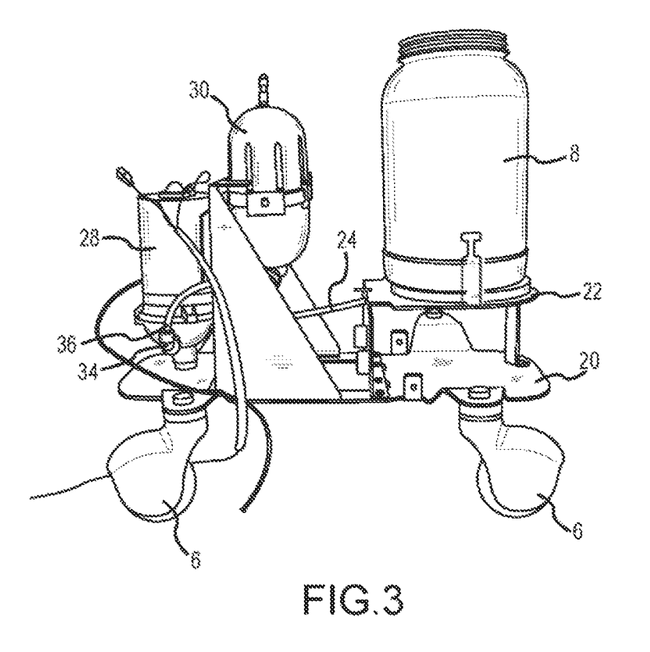
FIG. 3 is a side elevation view of a spray apparatus according to one embodiment of the present invention.

FIG. 3 is a side elevation view of the embodiment of FIG. 2 and taken from the opposing side as FIG. 2. As shown, the accumulator 30 is supplied with fluid by the pump 28, the pump outlet 34, and accumulator supply line 32. The pump provides fluid and pressure to the accumulator 30 via accumulator supply line 32. In one embodiment, the accumulator 30 comprises an accumulator having a maximum capacity of approximately 125 PSI. The accumulator may comprise known or pre-existing devices, such as the SHURFLO® Model No. 181-201, a 21 ounce capacity accumulator with a maximum working pressure of approximately 125 PSI. The accumulator 30 is operable to reduce pump cycling and provides consistent pressure to limit harmful pressure spikes and provide an even, desirable application of a disinfectant, for example. The accumulator 30 provides distinct advantages over known devices which apply inconsistent and erratic pressures and distributions of a liquid.

An accumulator outlet 46 is connected to the fluid exit line 40 to provide fluid to a dispensation device, such as a spray gun. The pump 28 and accumulator 30 are provided on an internal frame structure 32, provided in fixed relative position in the depicted embodiment. Preferably, the tank 8 is provided at a higher elevation than the pump 28 such that fluid can be gravity fed to an inlet of the pump 28. In various embodiments, the accumulator 30 comprises a pressure sensor or similar device for automatic activation and deactivation of the pump, and to maintain an internal pressure of the accumulator between a desired range. In alternative embodiments, the pressure sensor is provided in the pump. In various embodiments, such desired range is between approximately 20 and 250 PSI. In preferred embodiments, such desired range is between approximately 75 and 150 PSI. In some embodiments, the desired range is between approximately 75 PSI and 125 PSI. In a more preferred embodiment, such desired range is between approximately 85 and 120 PSI. In another preferred embodiment, the desired range is between approximately 85 PSI and 110 PSI.

As noted above, a device such as a pressure sensor may activate the pump to maintain a desired pressure range within the accumulator. In some embodiments, the trigger pressure is the lower bounds of any of the above desired pressure ranges for the accumulator. In various embodiments, the trigger pressure is between approximately 80 PSI and 90 PSI. In some embodiments, the trigger pressure is approximately 85 PSI.

Figure 4:
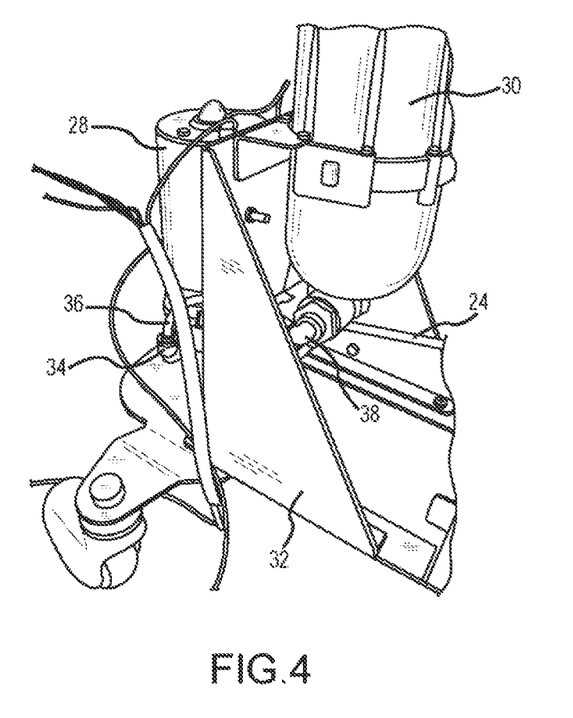
FIG. 4 is a perspective view of components of a spray apparatus according to one embodiment of the present invention.

FIG. 4 is a detailed perspective view of the embodiment of FIG. 3 showing the connection between the pump supply line 24, the pump 28, the pump outlet 34, the accumulator supply line 36, the accumulator inlet 38, and the accumulator 30. The accumulator is provided in a desired position on the internal frame structure 32 and, in at least one embodiment, secured thereto to prevent noise and vibration. Such vibration reduction may be accomplished by center-bonded rubber bushings, rubber mounts, rubber couplings, rubber grommets, or any other similar device commonly known in the art.

Figure 5:
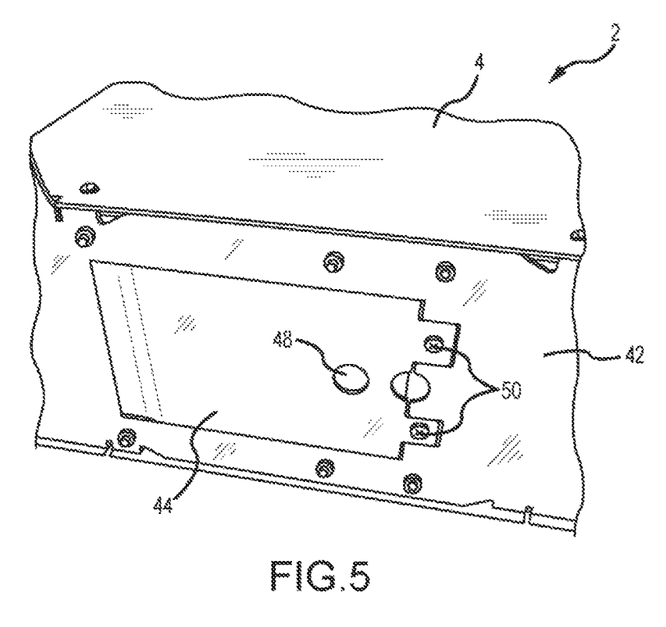
FIG. 5 is a perspective view of components of a spray apparatus according to one embodiment of the present invention.

FIG. 5 is a bottom view of the apparatus 2 according to one embodiment wherein the body 4 comprises a bottom surface 42, the bottom surface 42 comprising an access door 44 to access internal components including, for example, a battery. The door 44 comprises a user-grasping portion 48 and fasteners 50. The door 44 thus provides for relative ease of access to internal components that may need to be cleaned, repaired, replaced, etc.

Figure 6:
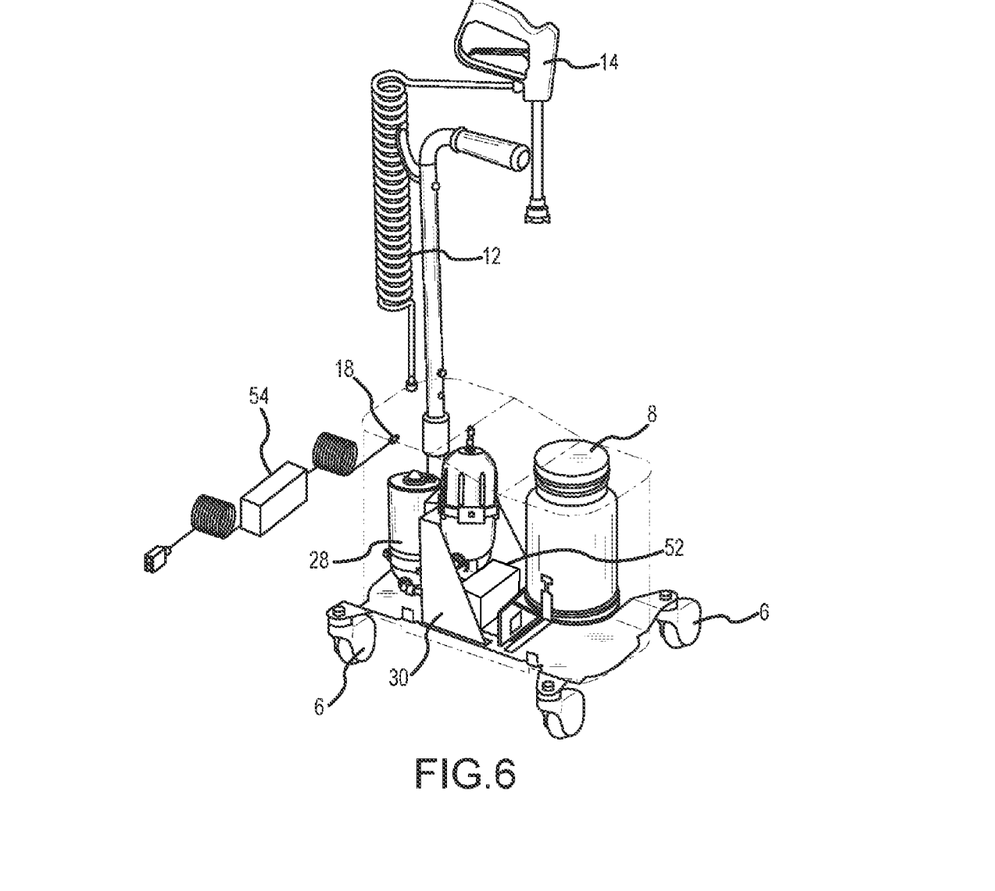
FIG. 6 is a perspective view of a spray apparatus according to one embodiment of the present invention, with certain components provided in phantom.

FIG. 6 is a perspective view of an apparatus 2 according to one embodiment. The apparatus 2 comprises a pump 28, an accumulator 30, a battery 52 for powering the pump, a tank 8 for housing clean fluid, a charging port 18 for charging the battery, a charger 54 connectable to a power source on one side and the battery on the other, a hose 12 and a spray gun 14 or wand. The unit 2 is provided on caster wheels 6 for facilitating movement of the device 2. As further shown in FIG. 7, the accumulator 30 and gun 14 of various embodiments comprise detachable, deployable features. The accumulator supply line 36 comprises a detachable coupling 56 that allows the accumulator 30 to maintain an internal pressure after detachment, and allows for increased portability of the accumulator 30 and the connected spray gun 14. In alternative embodiments, including those provided in FIGS. 2-3, the accumulator is not readily detachable from a remainder of the device 2 and is securely housed within the body 4.

Figure 7:
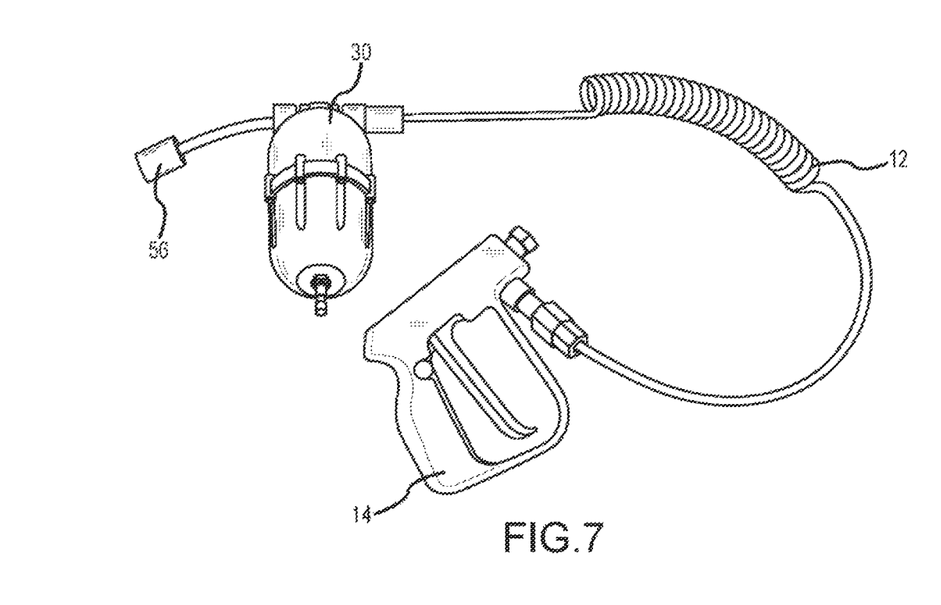
FIG. 7 is a perspective view of components of a spray apparatus according to one embodiment of the present invention.

The detachable coupling 56 has an attached state and a detached state. In the attached state, the coupling 56 allows for the free communication of fluid between the pump 28 and the accumulator 30. In the detached state, the coupling 56 prevents fluid communication between the pump 28 and the accumulator 30. Also, when the coupling 56 is in a detached state, the accumulator supply line 36 may separate such that the accumulator 30 and any downstream components are separable from the pump 28. Thus, a user may separate a charged accumulator 30 from the pump 28 and any chassis to use the present invention in challenging locations or hard-to-reach areas.

While various embodiments of the present invention have been described in detail, it is apparent that modifications and alterations of those embodiments will occur to those skilled in the art. However, it is to be expressly understood that such modifications and alterations are within the scope and spirit of the present invention. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A portable spray apparatus for use in dispensing a fluid, comprising:
    a body portion provided on a chassis, the chassis comprising a plurality of wheels adapted for conveying the apparatus;
    a clean fluid storage tank positioned at least partially within the body portion and having an internal volume to receive a fluid;
    a pump provided at least partially within the body portion, the pump comprising a fluid inlet in fluid communication with the clean fluid storage tank and a pump outlet in fluid communication with an accumulator;
    wherein the accumulator comprises a tank operable to maintain an internal pressure supplied by the pump, and wherein the accumulator is associated with a sensor operable to maintain the internal pressure of the accumulator between approximately 50 PSI and 150 PSI;
    wherein the accumulator is operable to reduce pump cycling and provide substantially consistent pressure to a spray gun;
    wherein the pump withdraws fluid from the clean fluid storage tank upon activation;
    a supply hose extending from the body portion and having a first end in fluid communication with the accumulator to receive the fluid;
    the spray gun connected to a second end of the supply hose; and
    a spray nozzle mounted to the spray gun, wherein the spray nozzle is sized to create a spray of fluid upon activation of the spray gun.

2. The portable spray apparatus of claim 1, wherein the device maintains the internal pressure of the accumulator between approximately 85 PSI and 110 PSI.

3. The portable spray apparatus of claim 1, further comprising:
    at least one usage sensor to monitor usage of the apparatus,
    a transmitter coupled to the at least one usage sensor, wherein the transmitter is configured to transmit data from the at least one usage sensor to a network; and
    a host system connected to the network and adapted to receive the at least one usage sensor data indicative of usage of the apparatus.

4. The portable spray apparatus of claim 1, wherein the pump activation is triggered by the internal pressure of the accumulator, wherein the trigger pressure is between approximately 80 PSI and 90 PSI.

5. The portable spray apparatus of claim 4, wherein the trigger pressure is approximately 85 PSI.

6. The portable spray apparatus of claim 1, wherein an accumulator supply line provides the fluid communication between the pump outlet and the accumulator, wherein the accumulator supply line comprises a detachable coupling.

7. The portable spray apparatus of claim 1, further comprising:
    a rechargeable battery provided within the body portion, wherein the rechargeable battery supplies power to the pump.

8. The portable spray apparatus of claim 7, wherein the rechargeable battery has a voltage rating, and the pump has a voltage rating, and wherein the battery voltage rating is between approximately 20% to 50% of the pump voltage rating.

9. The portable spray apparatus of claim 8, wherein the battery voltage rating is approximately 33% of the pump voltage rating.

10. A portable spray apparatus, comprising:
    a clean fluid storage tank having an internal volume to receive a fluid;

a pump comprising a fluid inlet in fluid communication with the clean fluid storage tank, and a pump outlet in fluid communication with an accumulator, wherein the accumulator comprises an inlet and an outlet, wherein the inlet of the accumulator is in fluid communication with the pump outlet, and the outlet of the accumulator is connected to a dispensation device, and wherein the accumulator comprises a tank which is operable to maintain an internal pressure supplied by the pump, wherein the pump withdraws the fluid from the clean fluid storage tank upon activation;

a detachable coupling disposed between the pump outlet and the accumulator, the detachable coupling having an attached state and a detached state, wherein in the attached state the coupling allows fluid communication between the pump outlet and the accumulator, and in the detached state the coupling prevents fluid communication between the pump outlet and the accumulator;

a supply hose having a first end in fluid communication with the accumulator to receive the fluid;

a spray gun connected to a second end of the supply hose;

a spray nozzle mounted to the spray gun, wherein the spray nozzle is sized to create a spray of fluid upon activation of the spray gun; and wherein the accumulator, supply hose, spray gun, and spray nozzle are separable from the pump when the coupling is in the detached state.

11. The portable spray apparatus of claim 10, further comprising:
a body portion provided on a chassis, the chassis comprising a plurality of wheels adapted for conveying the apparatus, wherein the clean fluid storage tank is positioned at least partially within the body portion, wherein the pump is provided within the body portion, and wherein the supply hose extends from the body portion.

12. The portable spray apparatus of claim 10, wherein the accumulator is associated with a device which maintains the internal pressure of the accumulator between approximately 50 PSI and 150 PSI.

13. The portable spray apparatus of claim 12, wherein the device maintains the internal pressure of the accumulator between approximately 85 PSI and 110 PSI.

14. The portable spray apparatus of claim 10, further comprising:
at least one sensor to monitor usage of the apparatus,
a transmitter coupled to the at least one sensor, wherein the transmitter is configured to transmit data from the at least one sensor to a network; and
a host system connected to the network and adapted to receive the at least one sensor data indicative of usage of the appliance.

15. The portable spray apparatus of claim 1, wherein the pump activation is triggered by the internal pressure of the accumulator, wherein the trigger pressure is between approximately 80 PSI and 90 PSI.

16. The portable spray apparatus of claim 15, wherein the trigger pressure is approximately 85 PSI.

17. The portable spray apparatus of claim 10, further comprising:
a rechargeable battery provided within the body portion, wherein the rechargeable battery supplies power to the pump.

18. The portable spray apparatus of claim 17, wherein the rechargeable battery has a voltage rating, and the pump has a voltage rating, and wherein the battery voltage rating is between approximately 20% to 50% of the pump voltage rating.

19. The portable spray apparatus of claim 18, wherein the battery voltage rating is approximately 33% of the pump voltage rating.

20. A portable spray apparatus for use in dispensing a fluid, comprising:
a body portion provided on a chassis, the chassis comprising a plurality of wheels adapted for conveying the apparatus;
a clean fluid storage tank positioned at least partially within the body portion and having an internal volume to receive a fluid;
a pump provided within the body portion, the pump comprising a fluid inlet in fluid communication with the clean fluid storage tank and a pump outlet in fluid communication with an accumulator comprising a tank and a diaphragm;
wherein an internal pressure of the accumulator is supplied by the pump, and wherein the accumulator is associated with a pressure sensor operable to maintain the internal pressure of the accumulator between approximately 85 PSI and 110 PSI;
wherein the pump withdraws a fluid from the clean fluid storage tank upon activation, wherein the activation is the internal pressure of the accumulator between approximately 85 PSI;
a rechargeable battery provided within the body portion, wherein the rechargeable battery supplies power to the pump, wherein the rechargeable battery has a voltage rating, and the pump has a voltage rating, and wherein the battery voltage rating is approximately 33% of the pump voltage rating;
a detachable coupling disposed between the pump outlet and the accumulator, the detachable coupling having an attached state and a detached state, wherein in the attached state the coupling allows fluid communication between the pump outlet and the accumulator, and in the detached state the coupling prevents fluid communication between the pump outlet and the accumulator;
a supply hose extending from the body portion and having a first end in fluid communication with the accumulator to receive the fluid;
a spray gun connected to a second end of the supply hose;
a spray nozzle mounted to the spray gun, wherein the spray nozzle is sized to create a spray of fluid upon activation of the spray gun; and
wherein the accumulator, supply hose, spray gun, and spray nozzle are separable from the pump when the coupling is in the detached state.

* * * * *